(12) United States Patent
Epstein et al.

(10) Patent No.: US 11,045,215 B2
(45) Date of Patent: *Jun. 29, 2021

(54) VASCULAR DEVICE VISIBILITY

(71) Applicant: Covidien LP, Mansfield, MA (US)

(72) Inventors: Evan Epstein, Costa Mesa, CA (US); Kenneth Brown, Oceanside, CA (US)

(73) Assignee: COVIDIEN LP, Mansfield, MA (US)

( * ) Notice: Subject to any disclaimer, the term of this patent is extended or adjusted under 35 U.S.C. 154(b) by 277 days.

This patent is subject to a terminal disclaimer.

(21) Appl. No.: 16/363,230

(22) Filed: Mar. 25, 2019

(65) Prior Publication Data

US 2019/0216475 A1 Jul. 18, 2019

Related U.S. Application Data

(63) Continuation of application No. 15/043,466, filed on Feb. 12, 2016, now Pat. No. 10,265,089.

(51) Int. Cl.
*A61B 17/221* (2006.01)
*A61B 90/00* (2016.01)
(Continued)

(52) U.S. Cl.
CPC ............ *A61B 17/221* (2013.01); *A61B 34/20* (2016.02); *A61B 90/39* (2016.02);
(Continued)

(58) Field of Classification Search
CPC ........ A61B 17/22031; A61B 17/22032; A61B 17/221; A61B 2017/22034;
(Continued)

(56) References Cited

U.S. PATENT DOCUMENTS 4,883,492 A 11/1989 Frey et al.
5,741,327 A 4/1998 Frantzen
(Continued)

FOREIGN PATENT DOCUMENTS

DE 102012109736 A1 2/2014
EP 0894481 A2 2/1999
(Continued)

OTHER PUBLICATIONS

Extended European Search Report dated Mar. 31, 2020; European Patent Application No. 19210104.6; 6 pages.

*Primary Examiner* — Wade Miles
*Assistant Examiner* — Kankindi Rwego
(74) *Attorney, Agent, or Firm* — Fortem IP LLP; Mary Fox; Derk Westermeyer

(57) ABSTRACT

A medical device can include an elongate manipulation member, and a thrombectomy device connected to the elongate manipulation member. The thrombectomy device can have a first configuration and a second configuration, the thrombectomy device being expandable from the first configuration to the second configuration. The thrombectomy device can include an arcuate marker-mounting projection attached to a portion of the thrombectomy device configured to contact a thrombus. A marker can be coupled to, and extending around, the arcuate marker-mounting projection with the marker and the arcuate marker-mounting projection contacting each other at three discrete locations. A method for engaging a thrombus can include advancing a thrombectomy device to a location radially adjacent to a thrombus in a blood vessel. The thrombectomy device can be positioned such that a marker, disposed at a proximal end of a working length of thrombectomy device, is proximal to or longitudinally aligned with a proximal end of the thrombus, and can be expanded into the thrombus.

18 Claims, 14 Drawing Sheets

(51) Int. Cl.
*A61B 34/20* (2016.01)
*A61B 17/22* (2006.01)
*A61F 2/82* (2013.01)

(52) U.S. Cl.
CPC .............. *A61B 2017/2215* (2013.01); *A61B 2017/22034* (2013.01); *A61B 2090/3966* (2016.02); *A61F 2/82* (2013.01); *A61F 2002/823* (2013.01)

(58) Field of Classification Search
CPC .. A61B 2017/22035; A61B 2017/2212; A61B 2017/2215; A61B 2017/2217; A61B 90/39; A61B 2090/3966; A61B 34/20; A61F 2/82; A61F 2002/823
USPC ........................................................ 606/200
See application file for complete search history.

(56) References Cited

U.S. PATENT DOCUMENTS

| | | | |
|---|---|---|---|
| 6,022,374 A | 2/2000 | Imran | |
| 6,066,149 A | 5/2000 | Samson et al. | |
| 6,234,177 B1 | 5/2001 | Barsch | |
| 6,251,135 B1 | 6/2001 | Stinson et al. | |
| 6,264,686 B1 | 7/2001 | Rieu et al. | |
| 6,264,689 B1 | 7/2001 | Colgan et al. | |
| 6,334,871 B1 | 1/2002 | Dor et al. | |
| 6,340,367 B1 | 1/2002 | Stinson et al. | |
| 6,402,777 B1 | 6/2002 | Globerman et al. | |
| 6,520,983 B1 | 2/2003 | Colgan et al. | |
| 6,669,722 B2 | 12/2003 | Chen et al. | |
| 6,679,911 B2 | 1/2004 | Burgermeister | |
| 6,699,278 B2 | 3/2004 | Fischell et al. | |
| 6,740,114 B2 | 5/2004 | Burgermeister | |
| 6,790,227 B2 | 9/2004 | Burgermeister | |
| 6,942,689 B2 | 9/2005 | Majercak | |
| 6,955,686 B2 | 10/2005 | Majercak et al. | |
| 6,998,060 B2 | 2/2006 | Tomonto | |
| 7,083,641 B2 | 8/2006 | Stinson et al. | |
| 7,083,822 B2 | 8/2006 | Brightbill | |
| 7,172,617 B2 | 2/2007 | Colgan et al. | |
| 7,179,273 B1 | 2/2007 | Palmer et al. | |
| 7,243,408 B2 | 7/2007 | Vietmeier | |
| 7,252,679 B2 | 8/2007 | Fischell et al. | |
| 7,300,458 B2 | 11/2007 | Henkes et al. | |
| 7,338,519 B2 | 3/2008 | Fischell et al. | |
| 7,357,813 B2 | 4/2008 | Burgermeister | |
| 7,594,927 B2 | 9/2009 | Majercak et al. | |
| 7,625,403 B2 | 12/2009 | Krivoruchko | |
| 7,761,138 B2 | 7/2010 | Wang et al. | |
| 7,771,464 B2 | 8/2010 | Brightbill | |
| 7,914,571 B2 | 3/2011 | Calisse | |
| 8,197,528 B2 | 6/2012 | Colgan et al. | |
| 8,285,363 B2 | 10/2012 | Malackowski et al. | |
| 8,357,178 B2 | 1/2013 | Grandfield et al. | |
| 8,357,179 B2 | 1/2013 | Grandfield et al. | |
| 8,398,596 B2 | 3/2013 | Field | |
| 8,409,270 B2 | 4/2013 | Clerc et al. | |
| 8,454,677 B2 | 6/2013 | Fischell et al. | |
| 8,491,647 B2 | 7/2013 | Colgan et al. | |
| 8,500,786 B2 | 8/2013 | Simpson et al. | |
| 8,500,787 B2 | 8/2013 | Simpson et al. | |
| 8,529,596 B2 | 9/2013 | Grandfield et al. | |
| 8,552,265 B1 | 10/2013 | Corbin | |
| 8,603,014 B2 | 12/2013 | Alleman et al. | |
| 8,632,584 B2 | 1/2014 | Henkes et al. | |
| 8,679,142 B2 | 3/2014 | Slee et al. | |
| 8,752,267 B2 | 6/2014 | Wu | |
| 8,752,268 B2 | 6/2014 | Wu | |
| 8,795,317 B2 | 8/2014 | Grandfield et al. | |
| 8,795,345 B2 | 8/2014 | Grandfield et al. | |
| 8,837,800 B1 | 9/2014 | Bammer et al. | |
| 8,852,265 B2 | 10/2014 | Clerc et al. | |
| 8,940,003 B2 | 1/2015 | Slee et al. | |
| 8,992,761 B2 | 3/2015 | Lin | |
| 9,038,260 B2 | 5/2015 | Wu | |
| 9,044,263 B2 | 6/2015 | Grandfield et al. | |
| 9,072,537 B2 | 7/2015 | Grandfield et al. | |
| 9,119,656 B2 | 9/2015 | Bose et al. | |
| 9,126,018 B1 | 9/2015 | Garrison | |
| 9,173,668 B2 | 11/2015 | Ulm | |
| 9,186,267 B2 | 11/2015 | Losordo et al. | |
| 9,211,132 B2 | 12/2015 | Bowman | |
| 9,233,015 B2 | 1/2016 | Geusen et al. | |
| 9,241,699 B1 | 1/2016 | Kume et al. | |
| 9,265,512 B2 | 2/2016 | Garrison et al. | |
| 9,308,007 B2 | 4/2016 | Cully et al. | |
| 9,399,118 B2 | 7/2016 | Kume et al. | |
| 9,445,828 B2 | 9/2016 | Turjman et al. | |
| 9,445,829 B2 | 9/2016 | Brady et al. | |
| 9,492,637 B2 | 11/2016 | Garrison et al. | |
| 9,539,022 B2 | 1/2017 | Bowman | |
| 9,561,345 B2 | 2/2017 | Garrison et al. | |
| 9,579,119 B2 | 2/2017 | Cully et al. | |
| 9,585,741 B2 | 3/2017 | Ma | |
| 9,642,635 B2 | 5/2017 | Vale et al. | |
| 9,655,633 B2 | 5/2017 | Leynov et al. | |
| 9,737,318 B2 | 8/2017 | Monstadt et al. | |
| 9,770,251 B2 | 9/2017 | Bowman et al. | |
| 9,801,643 B2 | 10/2017 | Hansen et al. | |
| 9,861,783 B2 | 1/2018 | Garrison et al. | |
| 9,993,257 B2 | 6/2018 | Losordo et al. | |
| 10,028,782 B2 | 7/2018 | Orion | |
| 10,029,008 B2 | 7/2018 | Creighton | |
| 10,039,906 B2 | 8/2018 | Kume et al. | |
| 2002/0058988 A1 | 5/2002 | Fischell et al. | |
| 2002/0058989 A1 | 5/2002 | Chen et al. | |
| 2002/0072792 A1 | 6/2002 | Burgermeister et al. | |
| 2002/0121497 A1 | 9/2002 | Tomonto | |
| 2002/0123796 A1 | 9/2002 | Majercak et al. | |
| 2002/0123797 A1 | 9/2002 | Majercak | |
| 2003/0040789 A1 | 2/2003 | Colgan et al. | |
| 2003/0050688 A1 | 3/2003 | Fischell et al. | |
| 2003/0069630 A1 | 4/2003 | Burgermeister et al. | |
| 2003/0204245 A1 | 10/2003 | Brightbill | |
| 2003/0225448 A1 | 12/2003 | Gerberding | |
| 2004/0015229 A1 | 1/2004 | Fulkerson et al. | |
| 2004/0102836 A1 | 5/2004 | Fischell et al. | |
| 2004/0167455 A1 | 8/2004 | Smart | |
| 2005/0004657 A1 | 1/2005 | Burgermeister | |
| 2005/0060025 A1 | 3/2005 | Mackiewicz et al. | |
| 2005/0172471 A1 | 8/2005 | Vietmeier | |
| 2005/0209678 A1 | 9/2005 | Henkes et al. | |
| 2006/0036312 A1 | 2/2006 | Tomonto | |
| 2006/0235507 A1 | 10/2006 | Brightbill | |
| 2006/0282111 A1* | 12/2006 | Morsi | A61M 25/1002 606/194 |
| 2007/0118206 A1 | 5/2007 | Colgan et al. | |
| 2007/0233237 A1 | 10/2007 | Krivoruchko | |
| 2011/0009941 A1 | 1/2011 | Sanders et al. | |
| 2012/0259404 A1 | 10/2012 | Tieu et al. | |
| 2013/0030461 A1 | 1/2013 | Marks et al. | |
| 2013/0079796 A1* | 3/2013 | Slee | A61B 17/221 606/127 |
| 2013/0116774 A1 | 5/2013 | Strauss et al. | |
| 2013/0131690 A1 | 5/2013 | Nagl et al. | |
| 2013/0281788 A1 | 10/2013 | Garrison | |
| 2013/0325104 A1 | 12/2013 | Wu | |
| 2013/0325105 A1 | 12/2013 | Wu | |
| 2013/0325106 A1 | 12/2013 | Wu | |
| 2013/0325107 A1 | 12/2013 | Wu | |
| 2013/0331926 A1 | 12/2013 | Wu | |
| 2014/0088678 A1 | 3/2014 | Wainwright et al. | |
| 2014/0094901 A1 | 4/2014 | Lorenzo et al. | |
| 2014/0194911 A1 | 7/2014 | Johnson et al. | |
| 2014/0194919 A1 | 7/2014 | Losordo et al. | |
| 2014/0200608 A1 | 7/2014 | Brady et al. | |
| 2014/0237801 A1 | 8/2014 | Wu | |
| 2014/0276074 A1 | 9/2014 | Warner | |
| 2014/0288637 A1 | 9/2014 | Clerc et al. | |
| 2014/0343595 A1 | 11/2014 | Monstadt et al. | |
| 2014/0343596 A1 | 11/2014 | Slee et al. | |
| 2014/0371779 A1 | 12/2014 | Vale et al. | |

(56) References Cited

U.S. PATENT DOCUMENTS

| | | |
|---|---|---|
| 2014/0371780 A1 | 12/2014 | Vale et al. |
| 2014/0371839 A1 | 12/2014 | Henkes et al. |
| 2015/0018934 A1 | 1/2015 | Pacetti |
| 2015/0045875 A1 | 2/2015 | Hingston et al. |
| 2015/0080937 A1 | 3/2015 | Davidson |
| 2015/0164523 A1 | 6/2015 | Brady et al. |
| 2015/0196693 A1 | 7/2015 | Lin |
| 2015/0313617 A1 | 11/2015 | Grandfield et al. |
| 2015/0359547 A1 | 12/2015 | Vale et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0296690 A1 | 10/2016 | Kume et al. |
| 2016/0302808 A1 | 10/2016 | Loganathan et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0231742 A1 | 8/2017 | Epstein et al. |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |
| 2019/0216475 A1 | 7/2019 | Epstein et al. |

FOREIGN PATENT DOCUMENTS

| | | |
|---|---|---|
| EP | 1488763 A2 | 12/2004 |
| EP | 1532943 A2 | 5/2005 |
| EP | 1515663 B1 | 10/2011 |
| EP | 2319575 B1 | 11/2013 |
| JP | 2014004219 A | 1/2014 |
| JP | 2018118132 A | 8/2018 |
| KR | 20180102877 A | 9/2018 |
| WO | 9707752 A1 | 3/1997 |
| WO | 9733534 A1 | 9/1997 |
| WO | 9930643 A1 | 6/1999 |
| WO | 9949812 A2 | 10/1999 |
| WO | 0224111 A2 | 3/2002 |
| WO | 03090810 A1 | 11/2003 |
| WO | 03101343 A1 | 12/2003 |
| WO | 2004008991 A1 | 1/2004 |
| WO | 2005028014 A1 | 3/2005 |
| WO | 2005082282 A1 | 9/2005 |
| WO | 2008041094 A2 | 4/2008 |
| WO | 2008101987 A1 | 8/2008 |
| WO | 2008130530 A1 | 10/2008 |
| WO | 2008141336 A1 | 11/2008 |
| WO | 2009105710 A1 | 8/2009 |
| WO | 2011006013 A1 | 1/2011 |
| WO | 2014011215 A1 | 1/2014 |
| WO | 2014052149 A1 | 4/2014 |
| WO | 2014139845 A1 | 9/2014 |
| WO | 2014140092 A2 | 9/2014 |
| WO | 2015021402 A1 | 2/2015 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

\* cited by examiner

VASCULAR DEVICE VISIBILITY

CROSS REFERENCE TO RELATED APPLICATION(S)

The present application is a continuation of U.S. application Ser. No. 15/043,466, filed Feb. 12, 2016, which is incorporated herein by reference in its entirety.

BACKGROUND OF THE DISCLOSURE

Blood vessels can become occluded by emboli, e.g., thrombi. For example, intracranial arteries can become occluded by thromboembolisms. Disruption of blood flow by the occlusion can prevent oxygen and nutrients from being delivered to tissues downstream of the occlusion. Deprivation of oxygen and nutrients to tissue distal to an occlusion can impair proper function of the tissue, and may result in cellular death. Cellular death increases with duration of the occlusion.

SUMMARY OF THE DISCLOSURE

Markers can be used to assist an operator in determining the location and/or orientation of a medical device within a blood vessel. Some aspects of the subject technology relate to attachment of a marker to a thrombectomy or other medical device. Some aspects of the subject technology relate to the positioning of one or more markers on a thrombectomy device. Some aspects of the subject technology relate to the use of markers in methods for removing thrombus from a blood vessel.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, 12, 16, or 24. The other clauses can be presented in a similar manner.

1. A medical device comprising:
    an elongate manipulation member; and
    a thrombectomy device connected to the elongate manipulation member, the thrombectomy device having a first configuration and a second configuration, the thrombectomy device being expandable from the first configuration to the second configuration; the thrombectomy device comprising a plurality of arcuate marker-mounting projections each attached to a portion of the thrombectomy device configured to contact a thrombus and arranged such that any laterally aligned arcuate marker-mounting projections are disposed laterally farther from each other when the thrombectomy device is in the second configuration than they are when the thrombectomy device is in the first configuration.

2. The medical device of clause 1, wherein each of the arcuate marker-mounting projections comprises a concave surface.

3. The medical device of clause 2, wherein the concave surface faces away from the portion of the thrombectomy device configured to contact the thrombus to which the arcuate marker-mounting projection is attached.

4. The medical device of clause 2, wherein each of the arcuate marker-mounting projections comprises a convex surface opposite the concave surface.

5. The medical device of clause 4, wherein the convex surface is parallel to the concave surface.

6. The medical device of clause 1, wherein the thrombectomy device comprises a plurality of struts forming a plurality of cells, and each of the arcuate marker-mounting projections extends from one of the struts.

7. The medical device of clause 6, wherein each of the arcuate marker-mounting projections is separated from all of the other arcuate marker-mounting projections by at least one strut length.

8. The medical device of clause 1, further comprising a plurality of markers, each marker being attached to only one of the arcuate marker-mounting projections.

9. The medical device of clause 1, wherein at least one of the marker-mounting projections is disposed at a proximal end of a working length of the thrombectomy device.

10. The medical device of clause 9, wherein the least one of the marker-mounting projection is within 5 millimeters of the proximal end of the working length.

11. The medical device of clause 1, wherein a group of marker-mounting projections is disposed at a proximal end of a working length of the thrombectomy device.

12. A medical device comprising:
    an elongate manipulation member;
    a thrombectomy device connected to the elongate manipulation member; an arcuate marker-mounting projection extending from a portion of the
    thrombectomy device configured to contact a thrombus; and
    a marker coupled to, and extending around, the arcuate marker-mounting projection with the marker and the arcuate marker-mounting projection contacting each other at three discrete locations.

13. The medical device of clause 12, wherein the marker and the marker-mounting projection contact each other at one location on a convex side of the arcuate marker-mounting projection, and the marker and the arcuate marker-mounting projection contact each other at two locations on a concave side of the marker-mounting projection.

14. The medical device of clause 13, wherein the one contact location on the convex side is between the two contact locations on the concave side.

15. The medical device of clause 13, wherein the convex side of the arcuate marker-mounting projection and the concave side of the marker-mounting projection are parallel.

16. A method for engaging a thrombus, the method comprising:
    (a) advancing a thrombectomy device, using an elongate manipulation member, to a location radially adjacent to a thrombus in a blood vessel, the thrombectomy device comprising a working length and a non-working length, the non-working length disposed between and separating the working length and a connection between the thrombectomy device and the elongate manipulation member, the working length having a proximal end and a distal end with a proximal marker disposed at the proximal end, and a distal marker, discrete from the proximal marker, disposed at the distal end;
    (b) positioning the thrombectomy device relative to the thrombus such that the proximal marker is proximal to or longitudinally aligned with a proximal end of the thrombus and the distal marker is distal to or longitudinally aligned with a distal end of the thrombus; and
    (c), after (b), expanding the thrombectomy device into the thrombus.

17. The method of clause 16, wherein a plurality of proximal markers are disposed at the proximal end of the working length and a plurality of distal markers are disposed at the distal end of the working length, and wherein positioning the thrombectomy device relative to the thrombus comprises positioning all of the proximal markers proximal to or longitudinally aligned with a proximal end of the thrombus and all of the distal markers distal to or longitudinally aligned with a distal end of the thrombus.

18. The method of clause 17, wherein a plurality of intermediate markers is attached to the thrombectomy device between the plurality of proximal markers and the plurality of distal markers, the method further comprising determining whether a maximum marker separation of the plurality of intermediate markers is less than a maximum marker separation of either the plurality of proximal markers or the plurality of distal markers.

19. The method of clause 18 wherein, when the maximum marker separation of the plurality of intermediate markers is not less than the maximum marker separation of either the plurality of proximal markers or the plurality of distal markers, the method further comprises:
   collapsing the thrombectomy device;
   repositioning the thrombectomy device relative to the thrombus such that the proximal marker is proximal to or longitudinally aligned with a proximal end of the thrombus and the distal marker is distal to or longitudinally aligned with a distal end of the thrombus; and
   re-expanding the thrombectomy device into the thrombus.

20. The method of clause 18 further comprising determining a state of expansion of the working length by observing the proximal, intermediate and distal pluralities of markers.

21. The method of clause 16, wherein the proximal marker is located within 5 millimeters of the proximal end of the working length.

22. The method of clause 21, wherein the thrombectomy device includes a plurality of cells, and wherein the proximal marker grouping is located within one cell-length of the proximal end of the working length.

23. The method of clause 21, wherein the thrombectomy device includes a generally cylindrical structure having a roll-up configuration.

24. A method for engaging a thrombus, the method comprising:
   advancing a thrombectomy device, using an elongate manipulation member, to a location radially adjacent to a thrombus in a blood vessel, the thrombectomy device comprising a working length having a proximal end and a distal end with a proximal marker disposed at the proximal end;
   positioning the thrombectomy device relative to the thrombus such that the proximal marker is proximal to or longitudinally aligned with a proximal end of the thrombus; and
   (c), after (b), expanding the thrombectomy device into the thrombus.

25. The method of clause 24, wherein the thrombectomy device further comprises a non-working length, the non-working length disposed between and separating the working length and a connection between the thrombectomy device and the elongate manipulation member, the proximal marker being located distal of the connection.

26. The method of clause 24, further comprising imaging the proximal end of the working length distinctly from the connection with the proximal marker.

27. The method of clause 24, wherein the thrombectomy device further comprises a distal marker, discrete from the proximal marker, disposed at the distal end of the working length.

28. The method of clause 27, further comprising positioning the thrombectomy device such that the distal marker is distal to or longitudinally aligned with a distal end of the thrombus.

29. The method of clause 27, wherein the thrombectomy device has a body comprising a plurality of struts, and the distal and proximal markers are more radiopaque than the body.

30. The method of clause 24, wherein a plurality of proximal markers are disposed at the proximal end of the working length, and wherein positioning the thrombectomy device relative to the thrombus comprises positioning all of the proximal markers proximal to or longitudinally aligned with a proximal end of the thrombus.

31. The method of clause 30, wherein a plurality of intermediate markers is attached to the thrombectomy device distal of the plurality of proximal markers, the method further comprising determining whether a maximum marker separation of the plurality of intermediate markers is less than a maximum marker separation of the plurality of proximal markers.

32. The method of clause 31, wherein, when the maximum marker separation of the plurality of intermediate markers is not less than the maximum marker separation of the plurality of proximal markers, the method further comprises:
   collapsing the thrombectomy device;
   repositioning the thrombectomy device relative to the thrombus such that the proximal marker is proximal to or longitudinally aligned with a proximal end of the thrombus; and
   re-expanding the thrombectomy device into the thrombus.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplifying and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION OF THE SUBJECT TECHNOLOGY

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology may be practiced without these specific details. In some instances, well-known structures and components are shown schematically to avoid obscuring the concepts of the subject technology.

Figure 1:
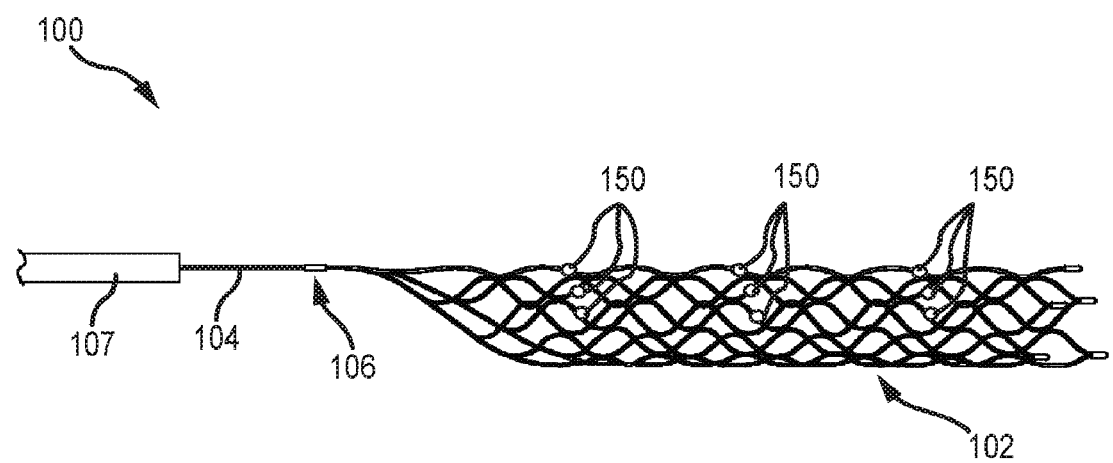
FIG. 1 illustrates a medical device including a thrombectomy device, according to an embodiment.

FIG. 1 depicts an exemplifying medical device 100 according to some embodiments of the subject technology. As illustrated in FIG. 1, the medical device 100 can comprise a vascular device or thrombectomy device 102 and a manipulation member 104. FIG. 1 also illustrates markers 150 attached to the thrombectomy device 102. A proximal end portion of the thrombectomy device 102 and a distal end portion of the manipulation member 104 can be joined at a connection 106. The manipulation member 104 can extend through a catheter 107 such that an operator can manipulate the thrombectomy device 102, positioned within and/or distal to a distal end of the catheter 107, using the manipulation member 104 at a location proximal to a proximal end of the catheter 107.

The manipulation member 104 can be an elongate manipulation member. The manipulation member 104 can have a length sufficient to extend from a location outside the patient's body through the vasculature to a treatment site within the patient's body. For example, the manipulation member can have a length of at least 100 cm, at least 130 cm, or at least 150 cm. The manipulation member 104 can be monolithic or formed of multiple joined components. In some embodiments, the manipulation member 104 can comprise a combination of wire(s), coil(s), and/or tube(s).

The thrombectomy device 102 and the manipulation member 104 can be attached together at the connection 106. In some embodiments, the thrombectomy device 102 and the manipulation member 104 can be substantially permanently attached together at the connection 106. That is, the thrombectomy device 102 and the manipulation member 104 can be attached together in a manner such that, under the expected use conditions of the medical device 100, the endovascular device and the manipulation member would not become separated, whether deliberately or unintentionally, from one another without damage to or destruction of at least a portion of the connection 106. In some embodiments, the thrombectomy device 102 and the manipulation member 104 can be permanently or releasably attached together at the connection 106.

In some embodiments, the connection 106 can comprise a marker. The marker of the connection can comprise a radiopaque material such as platinum, iridium, tantalum, gold, alloys thereof or bismuth and tungsten-doped polymers, among other materials. The connection marker can be more radiopaque than a body of the vascular or thrombectomy device 102. The connection marker can be visible under fluoroscopy, CAT scans, X-Rays, Mill, ultrasound technology or other types of imaging. The connection marker can include an interior channel, an interior recess or another mounting feature. Further, the connection marker can comprise a band or substantially cylindrical shape with an open or closed circumference, a coil, or other form.

It optionally may be advantageous to have a connection mechanism that permits intentional release of the thrombectomy device 102. For example, during a blood flow restoration procedure, it may prove difficult and/or dangerous to fully retrieve a thrombus due to a complicated vasculature or the risk of damaging a lumen wall. Leaving the thrombectomy device 102 inside the patient may prove to be the only option available to a surgeon or other medical personnel, or it may be a goal of the procedure, such as when the thrombectomy device 102 is deployed across an aneurysm (e.g., as an aneurysm bridge to retain coils or other materials in an aneurysm). In other circumstances the thrombectomy device 102 may include drug-eluting capabilities, and/or may be coated with a particular type of drug that facilitates thrombus dissolution. It may be advantageous in such circumstances to release the thrombectomy device 102 and allow the thrombectomy device 102 to anchor the thrombus against the lumen wall while the thrombus is dissolved by the drug. In some embodiments, the medical device 100 can comprise a portion, located proximally or distally of the connection 106, that is configured for selective detachment of the thrombectomy device 102 from the manipulation member 104. For example, such a portion can comprise an electrolytically severable or mechanically detachable segment of the manipulation member. In some embodiments, the medical device 100 can be devoid of any feature that would permit selective detachment of the thrombectomy device 102 from the manipulation member 104.

Figure 2:
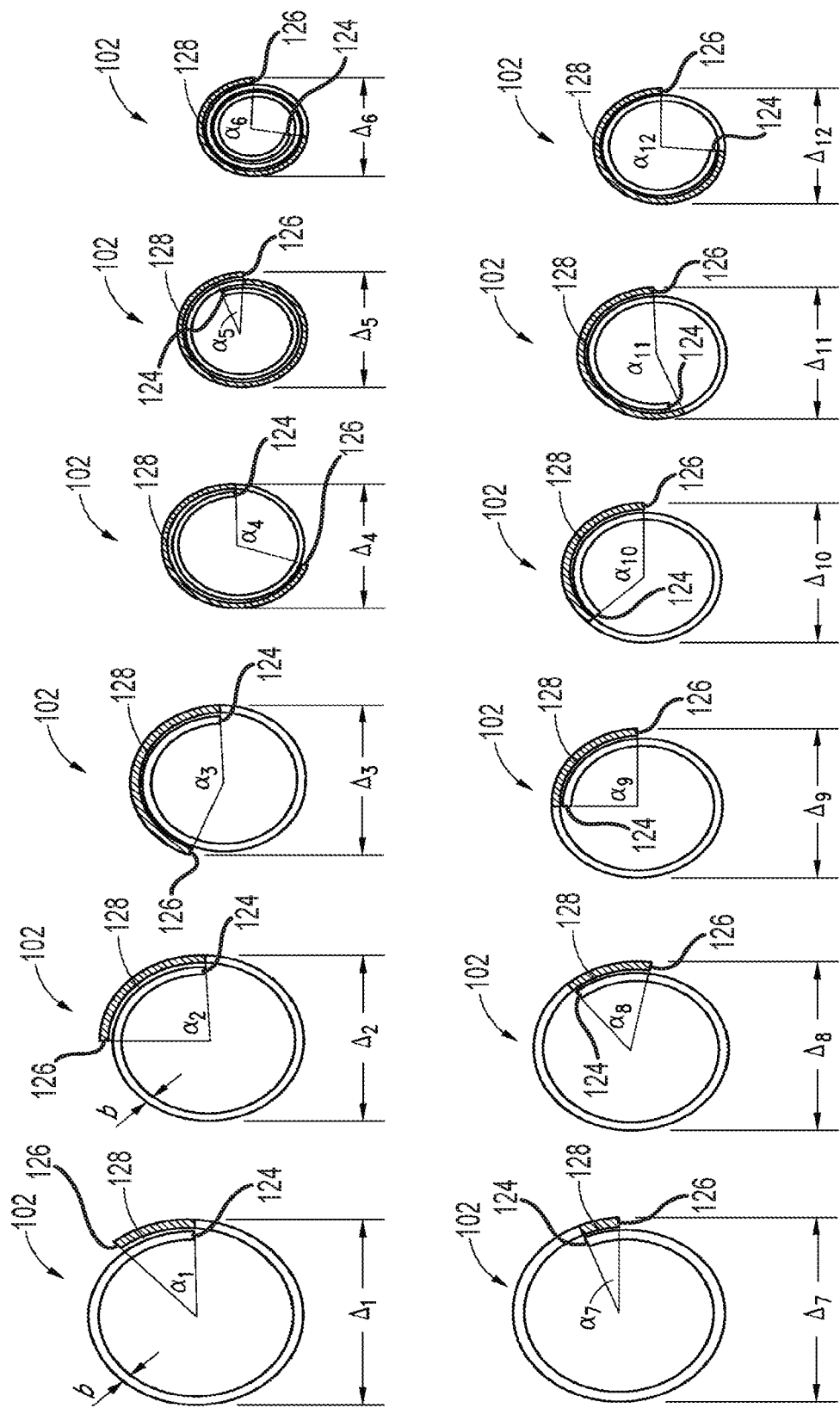
FIG. 2 is a schematic illustration of overlap configurations of the thrombectomy device of FIG. 1.

As illustrated in FIGS. 1 and 2, the thrombectomy device 102 can have a tubular or generally cylindrical shape in the absence of external forces in some embodiments. However, in some embodiments, the thrombectomy device can have a shape that is neither tubular nor cylindrical. In some embodiments, the thrombectomy device can have open proximal and distal ends, for example as illustrated in FIGS. 1 and 2, while in other embodiments, the thrombectomy device can have closed proximal and/or distal ends. In some embodiments, the thrombectomy device can comprise a series of structures (e.g., a longitudinal series of structures) each having proximal and distal ends that are open or closed. In some embodiments, the thrombectomy device can comprise a tubular or cylindrical structure disposed within, around, or radially overlapping such a series of structures or one or more other tubular or cylindrical structure(s). The thrombectomy device 102 can be self-expanding, e.g. by superelasticity or shape memory, or expandable in response to forces applied on the expandable member, e.g. by a balloon.

As shown in FIGS. 1 and 2, the thrombectomy device 102 in some embodiments can be curled, rolled, or otherwise formed such that a first edge 124 and a second edge 126 overlap one another, or form a gap between each other, when the thrombectomy device 102 is in a volume-reduced form. In a volume-reduced form, or an unexpanded form, the thrombectomy device 102 illustrated in FIGS. 1 and 2 can overlap itself to facilitate introduction of the thrombectomy device 102 into and through the catheter 107. FIG. 2 is a schematic illustration of overlap configurations (e.g., various amounts of overlap) of the thrombectomy device of FIG. 1. FIG. 2 illustrates various amounts of overlap of the thrombectomy device 102, forming zones of overlap 128. The thrombectomy device 102 can assume various diameters 41, 42, etc., depending on the degree of the overlap (e.g. represented by angle α1, α2, etc.). The extent of any overlap of a frame 108 of the vascular or thrombectomy device can depend upon a degree of the frame's expansion. Expansion within a vessel can be limited, at least in part, by the vessel's size, and the amount and the properties of any thrombus present. For example, a greater overlap of the edges 124, 126 can occur in narrower vessels, whereas in wider vessels the overlap can be smaller, or even an "underlap" may occur, in which case the edges 124 and 126 are separated by an open gap or space within the vessel. Advantageously, the presence of an overlap or "roll-up" configuration allows the thrombectomy device to be expanded or compressed in diameter with little or no change in length (e.g. foreshortening during expansion), in comparison to a similar device that lacks the overlap or roll-up configuration. This is because the expansion or compression can result from a decrease or increase in degree of overlap (see FIG. 2) rather than wholly from deformation of the struts 114 and cells 116 (FIG. 3), which deformation can decrease or increase the length of the device when transitioning to the expanded or compressed state.

In some embodiments, the thrombectomy device 102 is circumferentially continuous (e.g., forming a circumferentially continuous tubular or cylindrical shape), lacking first and second edges 124, 126 and having no overlap or gap in a volume-reduced form and expanded form. Regardless of whether the thrombectomy device is circumferentially continuous, the thrombectomy device 102 can have a central longitudinal axis both while in a volume-reduced form and when fully or partially expanded. In some embodiments, the thrombectomy device 102 can be self-expandable, and can expand toward a fully expanded configuration upon release from the catheter 107. Upon expansion, the thrombectomy device 102 can expand towards an inner wall of a vessel, towards an occlusive or partially-occlusive thrombus, clot or embolus within a vessel, or both.

The thrombectomy device 102 can be oversized relative to the interior of a vessel in which it is to be used, or the thrombectomy device 102 can occupy a larger volume when allowed to expand outside a vessel than when allowed to expand inside a vessel. In other words, the vessel may prevent a complete expansion of some or all of the thrombectomy device 102.

Upon thrombectomy device 102 expansion into an expanded configuration, portions of the thrombectomy device can to penetrate into a thrombus, capture a thrombus, or both. In some embodiments, the thrombectomy device 102 can capture the thrombus with an exterior, or radial exterior, of the expanded thrombectomy device 102. Additionally or alternatively, in some embodiments, the thrombectomy device 102 may contact, interlock, capture or engage with a portion of the thrombus with an interior, or radial interior, of the expanded thrombectomy device 102.

The thrombectomy device can comprise a working length and a non-working length. The portion of the thrombectomy device 102 in the working length is configured to interlock, capture or engage a thrombus. The portion of the thrombectomy device in the non-working length may contact thrombotic material in use, but is configured to perform a function that renders it ineffective or less effective other than the working length for interlocking, capturing or engaging with a thrombus. In some embodiments, the non-working length is disposed between the working length and the connection 106 to the manipulation member 104.

In some embodiments, the working length of the thrombectomy device 102 can comprise a repeating pattern of structural features. For example, a working portion of the thrombectomy device 102 illustrated in FIGS. 1 and 2 comprises a matrix of cells. Nonetheless, in some embodiments the repeating pattern of structural features can have other forms.

Figure 3:
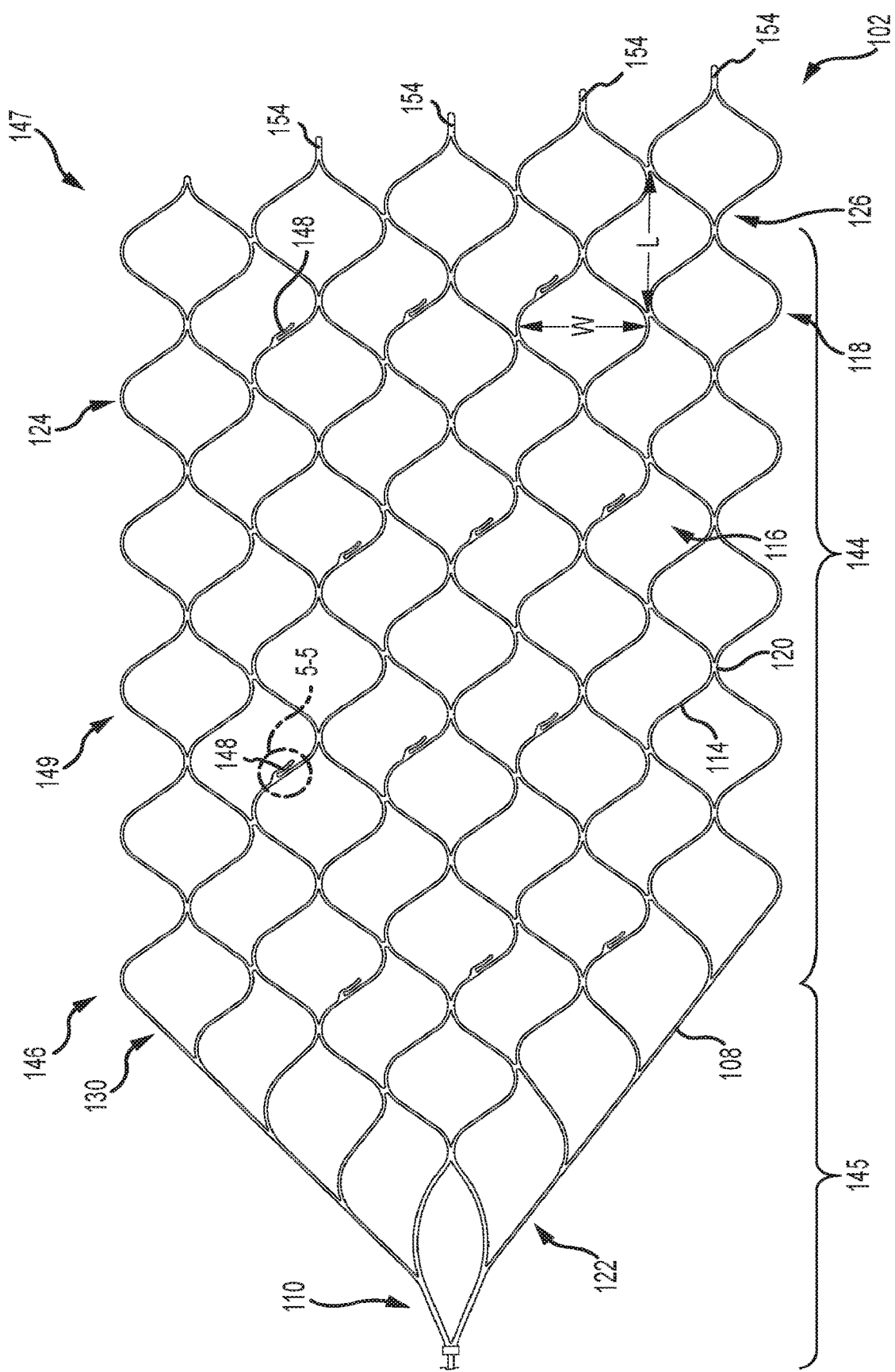
FIG. 3 illustrates an exemplifying thrombectomy device in an unrolled state.

FIG. 3 illustrates an exemplifying the vascular device or thrombectomy device 102 in a flat configuration to facilitate understanding of various features present in some thrombectomy devices according to various embodiments. The thrombectomy device 102 illustrated in FIG. 3 includes a working length 144 and a non-working length 145. As illustrated in FIG. 3, for example, the non-working length 145 is disposed between the working length 144 and the connection 106 to the manipulation member 104.

As illustrated in FIG. 3, in some embodiments, the thrombectomy device can comprise a frame or body 108 having a plurality of struts 114 and a plurality of cells 116, forming a mesh. Groups of longitudinally and serially interconnected struts 114 can form undulating members 118 that extend in a generally longitudinal direction. The struts 114 can be connected to each other by joints 120. While the struts are shown having a particular undulating or sinuous configurations, in some embodiments the struts can have other configurations. The frame of the thrombectomy device can have a generally tubular or generally cylindrical shape in some embodiments, while in others the frame can have a shape that is neither tubular nor cylindrical.

The working length 144 of the thrombectomy device illustrated in FIG. 3 comprises some of the cells 116. In embodiments wherein the thrombectomy device 102 comprises cells, the cells 116 in the working length and the portion of the thrombectomy device that form them can be sized and shaped such that they penetrate into a thrombus, capture a thrombus, or both upon expansion of the working length into a thrombus. In some embodiments, the portion of the thrombectomy device 102 in the working length can capture the thrombus with the individual cells 116 and/or with an exterior, or radial exterior, of the expanded thrombectomy device 102. Additionally or alternatively, in some embodiments, the portion of the thrombectomy device 102 in the working length may contact, interlock, capture or engage with a portion of the thrombus with individual cells 116 and/or an interior, or radial interior, of the expanded thrombectomy device 102.

As illustrated in FIG. 3, for example, the non-working length can comprise a tapered proximal portion 122 of the thrombectomy device 102. The proximal portion 122 of the thrombectomy device 102 can be tapered toward a proximal end 110 of the thrombectomy device 102. In some embodiments, the taper of the proximal, non-working portion 122 can advantageously facilitate retraction and repositioning of the medical device 100 and thrombectomy device 102. For example, in some embodiments, the non-working length 145 facilitates a retraction of the thrombectomy device 102 into the catheter 107.

In some embodiments, the tapered proximal, non-working portion 122 can be additionally or alternatively designed to generally not contact the vessel wall during a blood flow restoration procedure, and to generally not interfere with the flow of blood within a vessel.

The taper of proximal portion 122 can be at various angles relative to the manipulation member 104 or the longitudinal axis of the thrombectomy device 102. For example, in some embodiments, the taper can have an angle of approximately 45 degrees relative to the manipulation member, though other angles are also possible, and within the scope of the present disclosure.

The thrombectomy device 102 can comprise a first edge 124 and a second edge 126. The first edge 124 and second edge 126 can be formed, for example, from cutting a sheet or a tube. While the first and second edges are shown as having an undulating, or sinuous configuration, in some embodiments the first and second edges can have a straight, or linear configuration, or other configuration. In some embodiments, the edges 124, 126 can be curved, straight, or a combination thereof along the tapered proximal portion 122.

Each cell 116 of the thrombectomy device 102 can have a maximum length (labeled "L" in FIG. 3), as measured along a longitudinal axis of the thrombectomy device 102, and a maximum width W, as measured along a direction generally perpendicular to the length (labeled "W" in FIG. 3). FIG. 3 illustrates an embodiment of the thrombectomy device 102 having a pattern 130 of cells 116 of substantially uniform dimensions and struts 114 of substantially uniform dimensions. Nonetheless, in some embodiments, cell size and dimensions can vary along the length and wide of the frame 108, as can the individual filament thicknesses and widths.

FIG. 3 also illustrates a plurality of marker-mounting projections 148. Each marker-mounting projection 148 can be attached to a portion of the thrombectomy device 102 that may contact thrombus during use of the thrombectomy device. In some embodiments, the marker-mounting projections 148 can be attached to portions of the thrombectomy device 102 in the working length 144, for example as illustrated in FIG. 3. In embodiments wherein the thrombectomy device comprises struts 114, the marker-mounting projection(s) 148 can be attached to a strut 114. The marker-mounting projection 148 can be disposed within a cell 116, if present, or on another surface of the thrombectomy device 102. In some embodiments, a plurality of marker-mounting projections 148 can be attached respectively to a plurality of struts 114. In some embodiments, some or all of the marker-mounting projections 148 can each be attached to and/or at only a single strut 114. In some embodiments, the marker-mounting projection 148 can be attached to and/or at a joint 120. In some embodiments, the marker-mounting projections 148 can be separated from all other marker-mounting projections 148 by a distance, for example at least 2 mm or at least 3 mm, in a fully expanded configuration of the thrombectomy device 102. In some embodiments, the marker-mounting projections 148 can be separated from all other marker-mounting projections 148 by one cell width or one strut length (e.g., an entire length of a strut separates the adjacent marker-mounting projections).

One or more marker-mounting projections 148 can be located at some or all of a proximal end 146 of the working length 144, a distal end 147 of the working length 144, or an intermediate area 149 of the working length 144 between the proximal end 146 and the distal end 147. The working length 144 can extend continuously or intermittently between the proximal end 146 and the distal end 147.

In some embodiments, the proximal end of the working length can be at a proximalmost location where the thrombectomy device forms a complete circumference. In some embodiments, the proximal end of the working length can be at a proximalmost location where the thrombectomy device has its greatest transverse dimension in a fully expanded state. In some embodiments, the proximal end of the working length can be at a proximalmost location where the thrombectomy device has a peak, crown, or crest in transverse dimension in a fully expanded state.

In some embodiments, the distal end of the working length can be at a distalmost location where the thrombectomy device forms a complete circumference. In some embodiments, the distal end of the working length can be at a distalmost location where the thrombectomy device has its greatest transverse dimension in a fully expanded state. In some embodiments, the distal end of the working length can be at a distalmost location where the thrombectomy device has a peak, crown, or crest in transverse dimension in a fully expanded state.

In some embodiments, a marker-mounting projection 148 located at the proximal end 146 can be disposed within 5 mm, within 4 mm, within 3 mm, within 2 mm, or within 1 mm, proximally or distally, of the proximal end 146. In some embodiments, a marker-mounting projection 148 located at the proximal end 146 can be disposed within the length of one cell or one strut, proximally or distally, of the proximal end 146.

In some embodiments, a marker-mounting projection 148 located at the distal end 147 can be disposed within 5 mm, within 4 mm, within 3 mm, within 2 mm, or within 1 mm, proximally or distally, of the distal end 147. In some embodiments, a marker-mounting projection 148 located at the distal end 147 can be disposed within the length of one cell or one strut, proximally or distally, of the distal end 147.

A plurality or group of marker-mounting projections 148 can be located at some or all of the proximal end 146, the distal end 147, or the intermediate area 149. In some embodiments, the plurality or group of marker-mounting projections 148 at each of these locations (if present) have a common pattern. For example, the projections 148 in the plurality or group at the proximal end 146 can have the same arrangement relative to each other as do the projections 148 in the plurality or group at the distal end 147. The projections 148 in the plurality or group at intermediate area 149 (if present) can have the same arrangement relative to each other as do the projections 148 in the plurality or group at each of the proximal end 146 and the distal end 147, for example as illustrated in FIG. 3. In some embodiments, the marker-mounting projections 148 of such a plurality or group of marker-mounting projections 148 can be disposed farther from each other when the thrombectomy device 102 is in an expanded configuration that they are when the thrombectomy device 102 is in an unexpanded or less expanded configuration.

Figure 4:
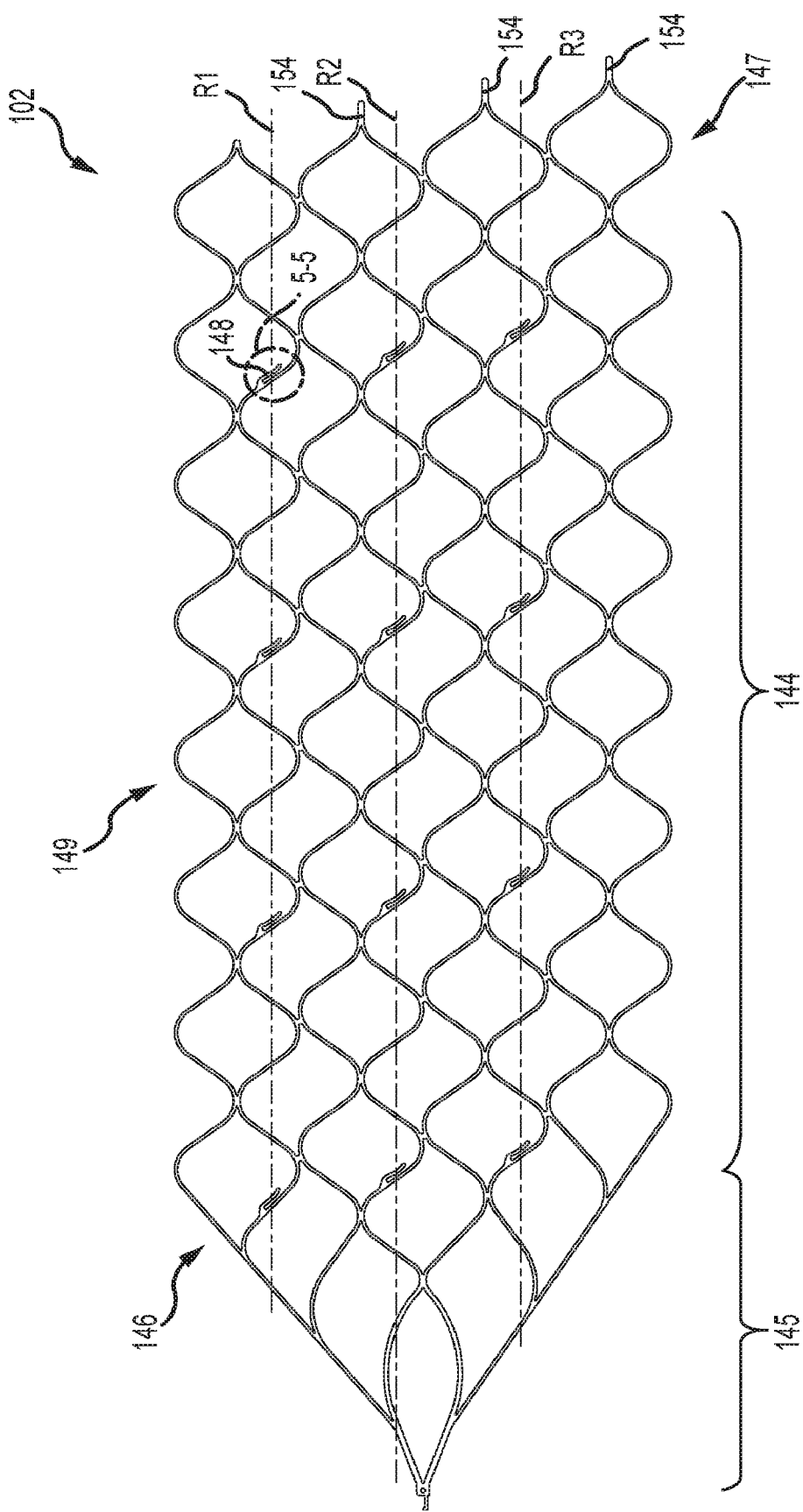
FIG. 4 illustrates another exemplifying thrombectomy device in an unrolled state.

In some embodiments, the vascular or thrombectomy device 102 can comprise one or more distally extending tips extending from a distal end of the thrombectomy device. For example, the device illustrated in FIG. 3 is shown comprising four elongate, distally extending tips 154 extending from a distal end of the thrombectomy device 102. In some embodiments wherein the thrombectomy device comprises struts, these distal tips 154 can extend from a distalmost row of struts, for example as illustrated in FIG. 3. In some embodiments, one or more markers 150 can be attached to the distal tips 154, if present. In some embodiments wherein one or more markers 150 are attached to the distal tips, the marker(s) 150 on the distal tips 154 can be positioned at the distal end 147 of the working length 144, for example as illustrated in FIG. 3. FIG. 4 illustrates another exemplifying the thrombectomy device 102 in a flat configuration to facilitate understanding of various features present in some thrombectomy devices according to various embodiments. FIG. 4 shows sets of marker-mounting projections 148 arranged or laterally aligned such that they lie along straight lines R1, R2, R3 that are parallel to a longitudinal axis of the thrombectomy device 102 in the absence of external forces on the thrombectomy device. However, when external forces are applied, the lines R1, R2, R3 through one or more of the sets of marker-mounting projections may not be straight and/or may not be parallel to the longitudinal axis of the thrombectomy device.

In some embodiments, the markers in a laterally aligned set or longitudinally grouped set can be separate and/or spaced from each other and from the markers in other sets and/or groups.

Figure 5:
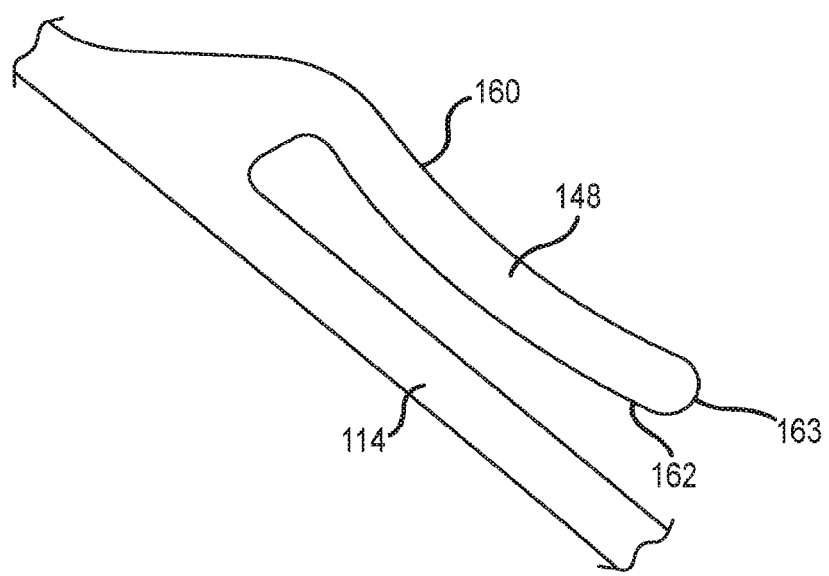
FIG. 5 is an enlarged view of a marker-mounting projection of the thrombectomy device shown in the area 5-5 of FIG. 4.
Figure 6:
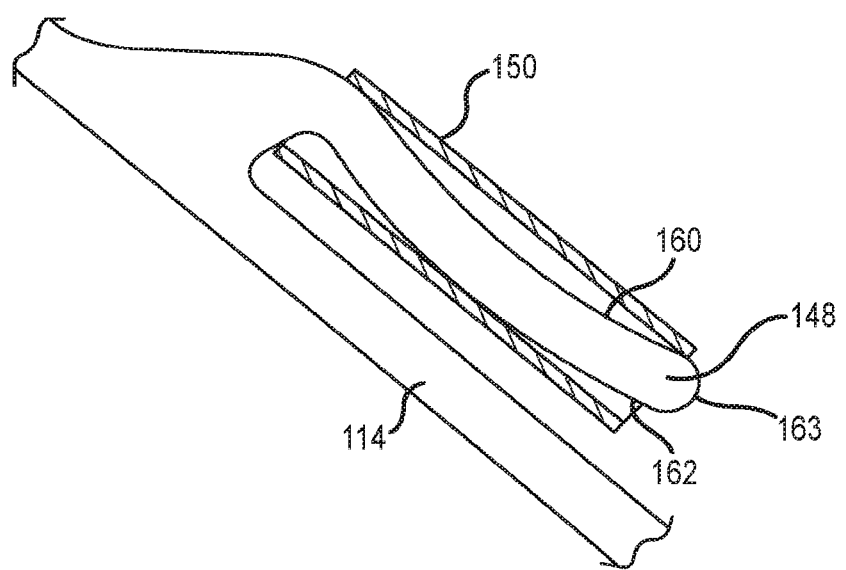
FIG. 6 illustrates the marker-mounting projection of FIG. 5 together with a marker.

FIGS. 5 and 6 are enlarged views of a marker-mounting projection 148 shown in the area 5-5 of FIG. 4. In some embodiments, the marker-mounting projection 148 has an arcuate, bowed or curved shape, and such a shape can span an entirety of the length of the marker-mounting projection 148 that receives a marker 150. In some embodiments, the marker-mounting projection 148 can be cantilevered from the portion of the thrombectomy device to which it is attached (e.g., from a strut 114, if present).

As illustrated in FIGS. 5 and 6, the marker-mounting projection 148 can include a concave surface 160 and a convex surface 162. However, some marker-mounting projections can have a concave surface 160 or a convex surface 162 (either without the other), or neither. In some embodiments, the concave surface 160 faces away from a portion of the thrombectomy device 102 to which to is attached (e.g., from a strut 114, if present). In some embodiments, the convex surface 162 is arranged opposite from the concave surface 160, facing toward a portion of the thrombectomy device 102 to which to is attached (e.g., toward a strut 114, if present), or both.

In some embodiments, the concave surface 160 and the convex surface 162 are parallel to each other over some or all of the length of the marker-mounting projection 148 that receives a marker 150. The marker-mounting projection 148 can comprise a constant cross-sectional area along its length and/or a constant width along the length of the marker-mounting projection 148 that receives a marker 150. In some embodiments, the concave surface 160, the convex surface 162, or both includes a constant curvature or radius along the length of the marker-mounting projection 148 that receives a marker 150. In some embodiments, the marker-mounting projection 148 includes a rounded distal end 163.

FIG. 6 illustrates a marker 150 on the marker-mounting projection 148. The marker 150 can comprise a radiopaque material such as platinum, iridium, tantalum, gold, alloys thereof or bismuth and tungsten-doped polymers, among other materials. The marker 150 can be more radiopaque than a body of the vascular or thrombectomy device 102. The marker 150 can be visible under fluoroscopy, CAT scans, X-Rays, Mill, ultrasound technology or other types of imaging. The marker 150 can include an interior channel, an interior recess or another mounting feature. Further, the marker 150 can comprise a band or substantially cylindrical shape with an open or closed circumference, a coil, or another form that mounts around a marker-mounting projection 148.

The marker 150 can directly attach to the marker-mounting projection 148 through direct contact between the marker 150 and the marker-mounting projection 148. In some embodiments, adhesives, welding, soldering, friction or mechanical fastening (e.g., crimping) directly attach the marker 150 to marker-mounting projection 148. In some embodiments, the marker 150 extends completely around the marker-mounting projection 148 when the marker 150 is mounted, or directly attached, to the marker-mounting projection 148. In another embodiment, the marker 150 extends partially (e.g., at least three quarters of the perimeter) around the marker-mounting projection 148 when the marker 150 is mounted, or directly attached, to the marker-mounting projection.

The marker-mounting projection 148 can extend generally parallel to a segment of the thrombectomy device (e.g., a strut) adjacent to the marker 150, for example as illustrated in FIG. 5, or such that a marker when mounted to the marker-mounting projection 148 is parallel to a segment of the thrombectomy device (e.g., a strut) adjacent to the marker 150, for example as illustrated in FIG. 6.

The marker 150 and the marker-mounting projection 148 can contact each other at three discrete locations when the marker 150 is directly attached to the marker mounting projection 148. In some embodiments, the marker 150 and the marker-mounting projection 148 contact each other at more or fewer than three locations when the marker 150 is directly attached to the marker mounting projection 148. In other embodiments, the marker 150 and the marker-mounting projection 148 contact each other at two locations on the concave surface 160 and at one location on the convex surface 162 when the marker 150 is directly attached to the marker-mounting projection 148. In one embodiment, the contact location of the marker 150 and the convex surface 162 is located between the contact locations of the marker 150 and the concave surface 160.

In some embodiments, an arcuate marker-mounting projection can have greater marker retention strength, better withstand electropolishing, or both compared to marker-mounting projection having a straight configuration.

Figure 7:
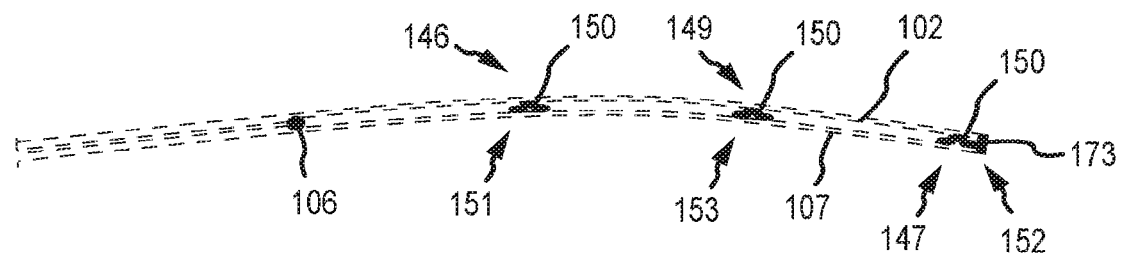
FIG. 7 is a schematic representation of a fluoroscopic image of an arrangement of markers when a thrombectomy device to which they are attached is in an unexpanded state.
Figure 8:
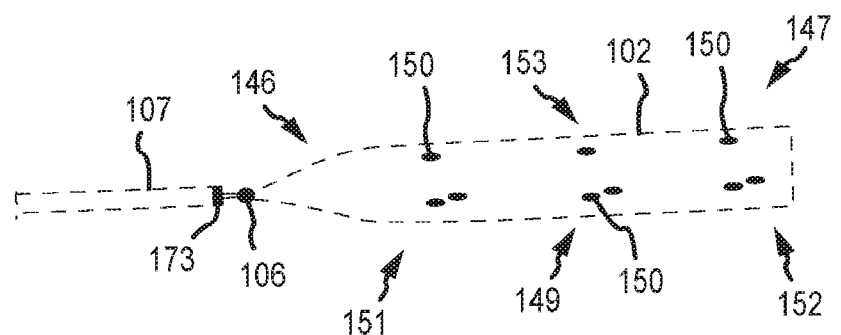
FIG. 8 is a schematic representation of a fluoroscopic image of the markers of FIG. 7 when the thrombectomy device to which they are attached is in a fully expanded state.
Figure 9:
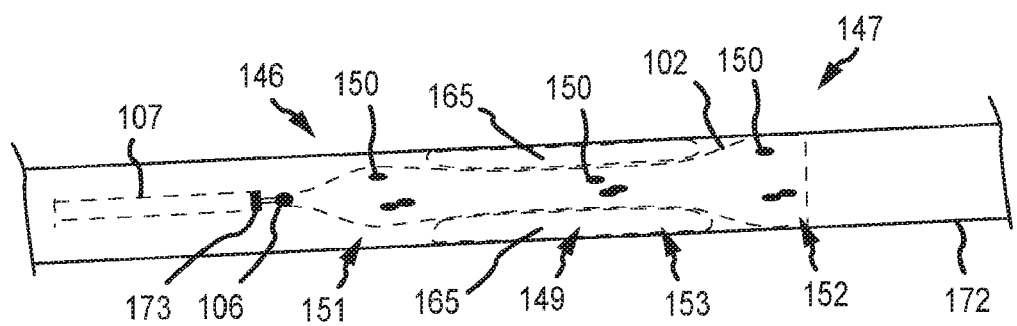
FIG. 9 is a schematic representation of a fluoroscopic image of the markers of FIG. 7 when the thrombectomy device to which they are attached is partially expanded within a vessel and in contact with a thrombus.

FIGS. 7-9 are schematic representations of fluoroscopic images of an arrangement of markers when a thrombectomy device to which they are attached is in various states. FIG. 7 illustrates an arrangement of markers 150 when the thrombectomy device 102 is in an unexpanded state within a catheter 107 (see FIG. 1). As shown in FIG. 7, the markers 150 in a proximal marker group 151, which can be located at the working length proximal end 146 and mounted on marker-mounting projections 148, markers 150 in a distal marker group 152, which can be located at the working length distal end 147 and mounted on marker-mounting projections 148, and markers 150 in an intermediate marker group 153, which can be located at the working length intermediate area 149 and mounted on marker-mounting projections 148, can be in close lateral proximity to the other markers 150 in the respective marker group. In some embodiments, a portion of a length of the thrombectomy device 102 between the proximal marker group 151 and the distal marker group 152, or between the working length proximal 146 and distal 147 ends, has no marker 150.

FIG. 8 illustrates the markers of FIG. 7 when the thrombectomy device 102 is in a fully expanded state. As shown in FIG. 8, the markers 150 in the proximal marker group 151, the markers 150 in the distal marker group 152, and the markers 150 in the intermediate marker group 153 can be located farther laterally from the other markers 150 in a respective marker group in this state than they are when the thrombectomy device 102 is in an unexpanded state. FIG. 8 also shows the markers having substantially the same pattern and/or spacing relative to each other in each of the proximal marker group 151, the distal marker group 152, and the intermediate marker group 153.

FIG. 9 illustrates the markers of FIG. 7 when the thrombectomy device 102 is in a partially expanded state within a vessel and in contact with a thrombus. As shown in FIG. 9, markers 150 in the intermediate marker group 153 are not spaced as far from each other laterally as are the markers 150 in the proximal marker group 151 from each other or the markers 150 in the distal marker group 152 are from each other. Such an arrangement can occur when the thrombectomy device 102 is in an expanded state in the presence of a thrombus 165 that inhibits or prevents expansion of a region of the thrombectomy device.

Figure 10:
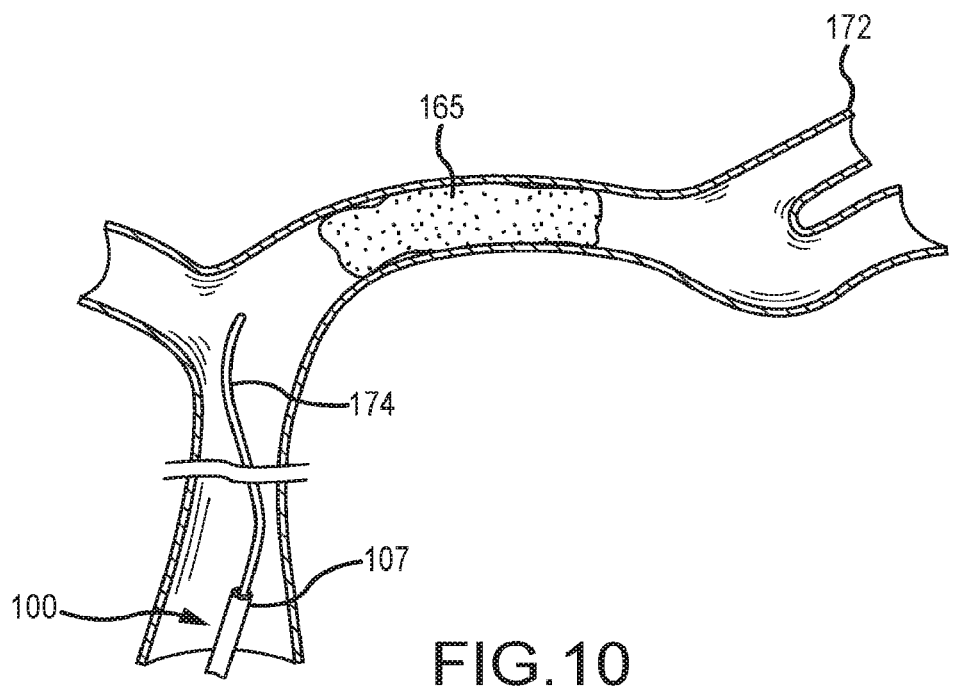
FIGS. 10-13 are cross-sectional views of a blood vessel and illustrate a processes of advancing and positioning a medical device, according to some embodiments.
Figure 11:
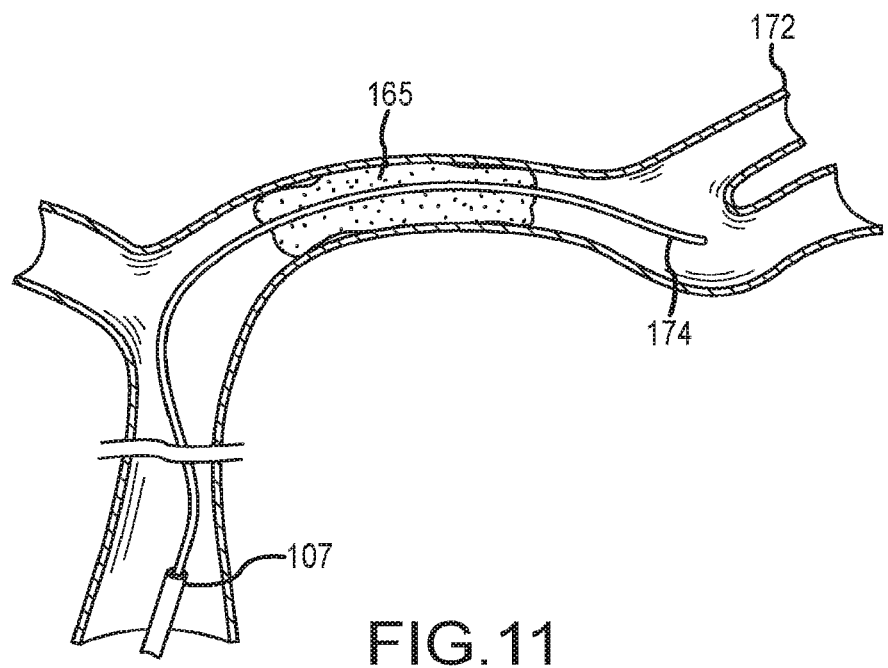
Figure 12:
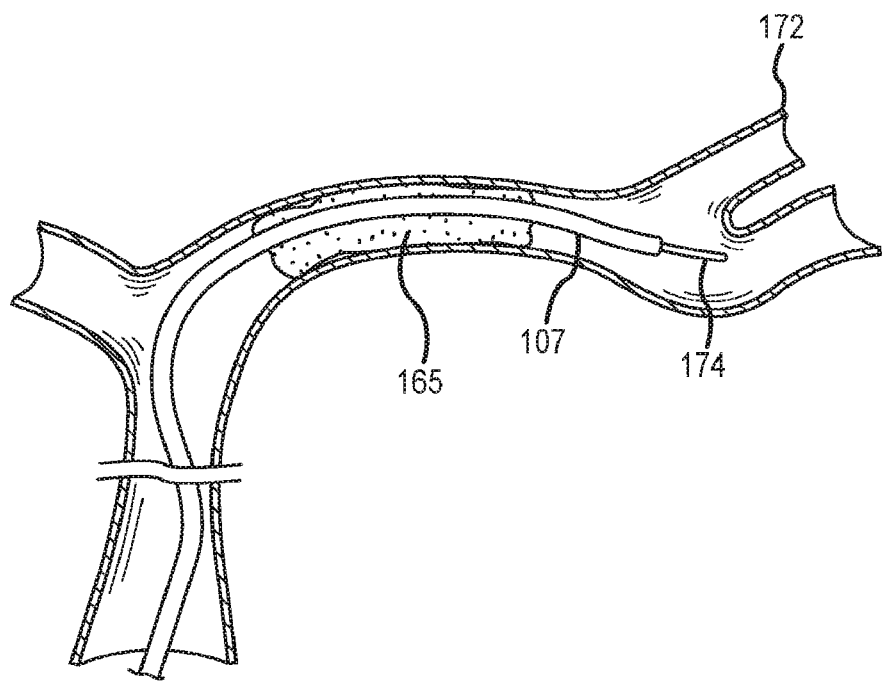

Methods for engaging and removing a thrombus 165 will now be discussed with reference to FIGS. 10-20. Referring to FIG. 10, the medical device 100 may be inserted into an anatomical vessel 172 by first inserting a guide wire 174 into the anatomical vessel 172. The illustrated anatomical vessel is an intracranial blood vessel. In some embodiments, the medical device is introduced into a segment of cerebral blood vessel distal to the carotid siphon. The inserted medical device 100 can be any embodiment of the medical device 100 disclosed herein, including any of the thrombectomy devices 102, elongate members 104, or connections 106. The guide wire 174 can be advanced through a guide catheter 164 (see FIG. 18), which optionally includes a balloon near the guide catheter's distal end, and/or a catheter 107 to the treatment site, adjacent the thrombus 165. Referring to FIG. 11, the guide wire 174 is advanced distally through the thrombus 165. Once the guide wire 174 is in position, the catheter 107 is advanced over the guide wire 174, through a distal end of the guide catheter, toward the thrombus 165 in the anatomical vessel 172. Referring to FIG. 12, the catheter 107 is advanced distally through the thrombus 165. The guide wire 174 is then withdrawn proximally.

Figure 13:
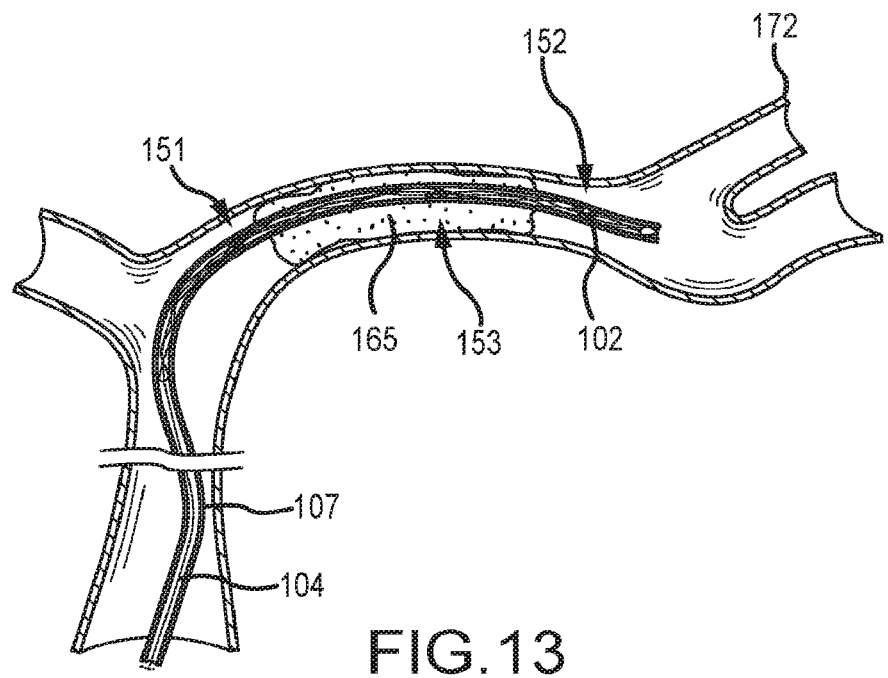

Referring to FIG. 13, the medical device 100 is advanced through the catheter 107. The medical device 100 is advanced through the catheter 107 by the manipulation member 104 coupled to the thrombectomy device 102 (e.g., at the proximal end of the thrombectomy device). The catheter 107 prevents expansion of the thrombectomy device 102 and thus maintains the thrombectomy device 102 in a compressed, volume-reduced configuration as the thrombectomy device 102 is advanced to the treatment site. The thrombectomy device 102 is advanced or otherwise moved to position (i) the proximal marker or marker group 151 proximal to a proximal end 170 of the thrombus 165, and (ii) the distal marker or marker group 152 distal to a distal end 171 of the thrombus 165. If an intermediate marker or marker group 153 is present, the thrombectomy device 102 is advanced or otherwise moved to position the intermediate marker or marker group 153 between the proximal and distal ends of (e.g., within) the thrombus.

Figure 14:
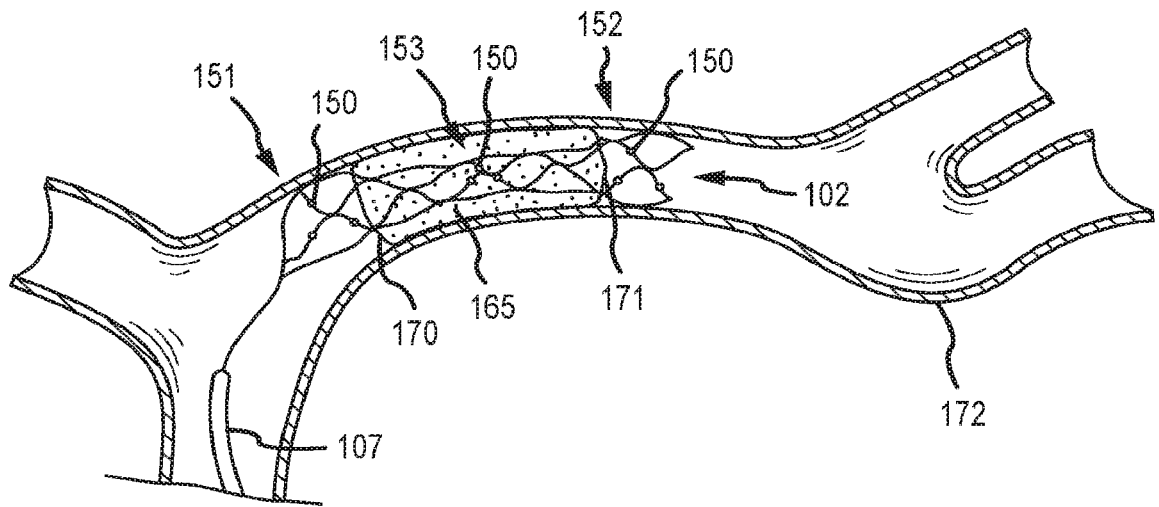
FIGS. 14-16 are cross-sectional views of the blood vessel shown in FIGS. 10-13, and illustrate various clot positions and thrombectomy device configurations, according to some embodiments.
Figure 17:
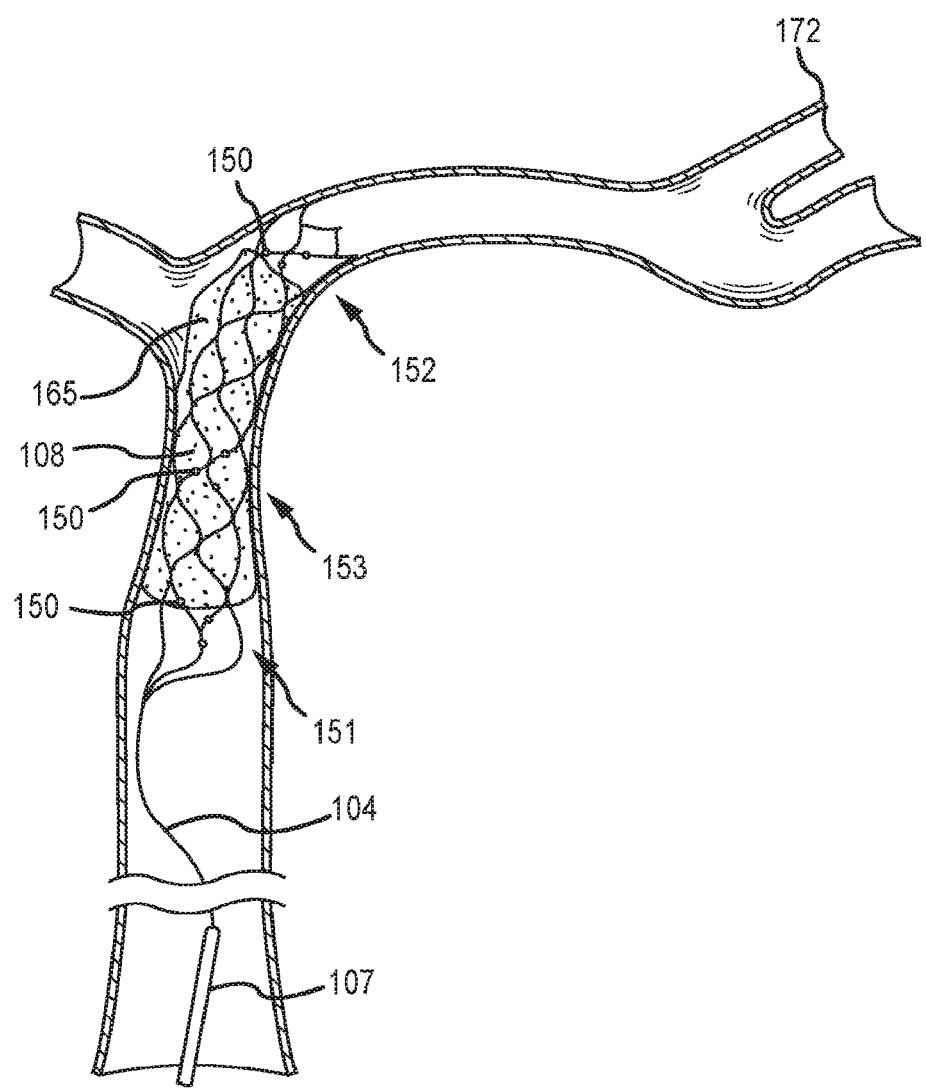
FIGS. 17-20 are cross-sectional views of a blood vessel and illustrate uses of a medical device according to some embodiments.

Turning to FIG. 14, the catheter 107 is then withdrawn proximally relative to the thrombectomy device 102 to expose the thrombectomy device 102. If the thrombectomy device 102 is self-expanding, retraction of the catheter 107 can permit the thrombectomy device 102 to expand to an expanded state. FIG. 14 illustrates the markers 150 of the proximal marker group 151 and the distal marker group 152 as more expanded than are the markers 150 of the intermediate 153 marker group, which appear in a less expanded distribution. Such an arrangement can result when the thrombectomy device 102 is expanded while all markers 150 of the proximal marker group 151 are located proximal to the thrombus 165, or to a proximal end of the thrombus 170, and all markers 150 of the distal marker group 152 are located distal to the thrombus 165, or to a distal end of the thrombus 171. When such a marker 150 arrangement is observed, an operator may check, by injecting contrast solution through the catheter 107 or guide catheter 164, for perfusion of the distal vasculature through the thrombus 165 via a flow channel (if any) opened in the thrombus 165 by the expansion of the thrombectomy device 102, allow the thrombectomy device 102 to continue expanding into the thrombus 165 and/or proceed to withdraw the thrombectomy device 102, as illustrated in FIG. 17.

Figure 15:
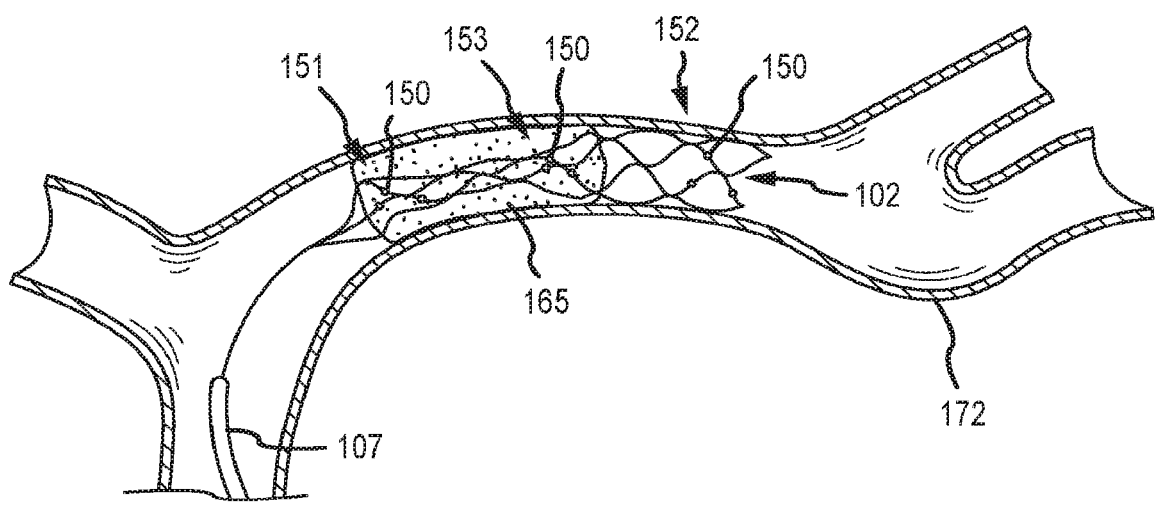

FIG. 15 illustrates another configuration of the thrombectomy device 102, wherein the markers 150 of the distal marker group 152 are more expanded than are the markers 150 of the proximal marker group 151 or the marker group intermediate 153, which each appear in a less expanded state. Such an arrangement can result when the thrombectomy device 102 is expanded while all markers in the proximal marker group 151 and the intermediate marker group 153 are located radially adjacent to the thrombus 165 within the blood vessel and all markers in the distal marker group 152 are located distal to the thrombus 165 or a distal end 171 of the thrombus. When such a marker 150 arrangement is observed, an operator may check for perfusion of the distal vasculature through the thrombus 165, allow the thrombectomy device 102 to continue expanding into the thrombus 165 and/or proceed to withdraw the thrombectomy device 102, as illustrated in FIG. 17.

Figure 16:
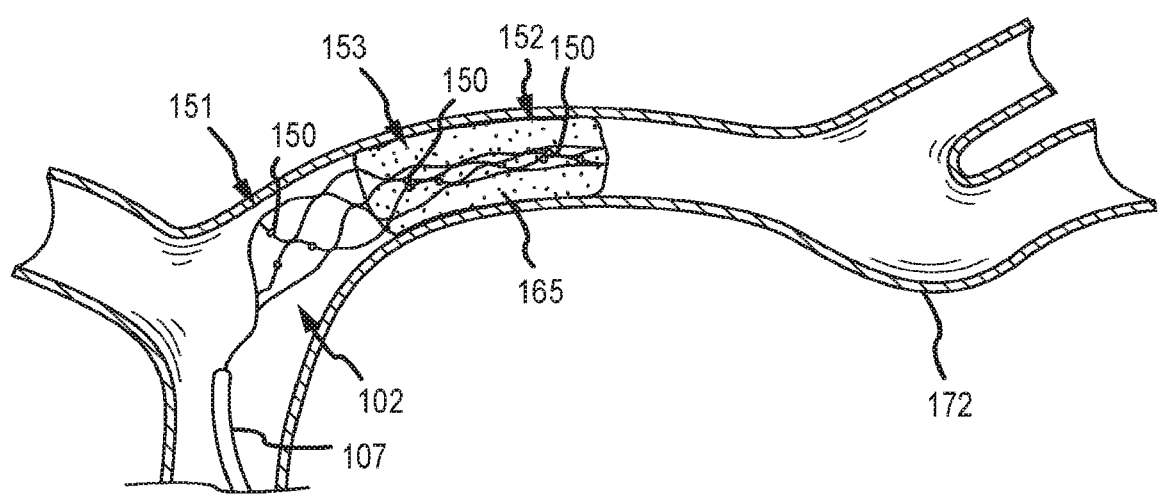

FIG. 16 illustrates another configuration of the thrombectomy device 102, wherein the markers 150 of the proximal marker group 151 are more expanded than are the markers 150 of the distal marker group 152 or intermediate marker group 153, which appear in less expanded state. Such an arrangement can result when the thrombectomy device 102 is expanded while the markers in the distal marker group 152 are not located distal to the thrombus 165 or a distal end 171 of the thrombus or when the thrombus migrates distally during or after expansion of the thrombectomy device 102.

When a marker 150 arrangement as illustrated in FIG. 16 is observed or determined, or when a maximum marker 150 separation of the intermediate marker group 153 is observed as greater than a maximum marker 150 separation of either the proximal marker group 151 or distal marker group 152, an operator may elect to collapse the thrombectomy device 102 into less unexpanded state, for example by advancing the catheter 107 over the thrombectomy device 102. The operator can then again position the thrombectomy device 102 relative to the thrombus and expand the thrombectomy device as described above.

With the proximal marker or marker group 151 located at the working length proximal end 146, the operator can more accurately and/or confidently position the thrombectomy device relative to a thrombus prior to expansion, thereby facilitating utilization of the working length of the thrombectomy device. In some embodiments, positioning the thrombectomy device 102 with reference to the proximal marker or marker group 151 located at the working length proximal end 146 can facilitate or promote a successful removal of the thrombus or clot 165, by achieving a more secure contact, interlock or engagement between the thrombectomy device 102 and the thrombus or clot 165. Further, a comparison of the relative extent of marker group expansion can provide information to an operator that assists in determining whether and how (e.g., which direction) to reposition the thrombectomy device 102.

Accordingly, during a revascularization procedure, the user can use the proximal marker group 151 and/or the distal marker group 152 to properly locate the thrombectomy device 102 longitudinally relative to the thrombus 165 before expanding the device 102 into the thrombus. At appropriate time(s) in the procedure, the user can establish the location of the thrombus on an image of the treatment location (such as a fluoroscopic image or other suitable image as disclosed herein) by injecting contrast media into the target vessel 172 and observing the effect of the thrombus on the flow of the contrast media in the vessel. Once the catheter 107 is positioned in the thrombus 165 as shown in FIG. 12, the user can advance the thrombectomy device 102 toward the distal end of the catheter and observe in the image of the treatment location the position of the proximal marker group 151 and/or the distal marker group 152 relative to the thrombus 165 (e.g. relative to the proximal end 170 and/or the distal end 171 thereof). This can be done while the thrombectomy device 102 is still in the catheter to enable adjustment of the position of the thrombectomy device 102 prior to expansion; FIG. 7 depicts an example of a fluoroscopic image that the user might observe with the proximal marker group 151 and the distal marker group 152 clearly visible due to their radiopacity. The user can also observe from such an image that the entire device 102 is still in the catheter 107 due to the closely "packed" state of the marker groups 151, 152, 153 (and as well that the distal end of device 102 is near the distal tip of the catheter 107 as may be facilitated by a catheter tip marker 173 (see FIGS. 7-9). With the location of the proximal end of the working length 144 indicated in the image by the proximal marker group 151 (and, optionally, the distal end of the working length 144 indicated in the image by the distal marker group 152), the user can determine whether the proximal end of the working length 144 is positioned proximal of or longitudinally aligned with the proximal end 170 of the thrombus (and, optionally, whether the distal end of the working length 144 is positioned distal of or longitudinally aligned with the distal end 171 of the thrombus). Based on this observation, the user can either confirm that the working length 144 of the device 102 is aligned with (or spans the entirety of) the length of the thrombus 165; if either or both is the case the user can leave the device in its current longitudinal position relative to the thrombus; if not, the user can adjust the longitudinal position of the device 102 until it is correctly positioned relative to the thrombus 165 as described above. Once the user has confirmed the correct positioning of the device 102 in this manner, the user can proceed to expand the device 102 into the thrombus 165, e.g. as described elsewhere herein, and remove some or all of the thrombus from the vessel 172. Advantageously, as mentioned above, when the thrombectomy device 102 is of an overlap or roll-up configuration, relatively little or no change in the length of the device 102 will occur during expansion, and accordingly the positions of the markers relative to the thrombus (and to each other) will not change significantly or at all as the device expands. This in turn facilitates accurate placement of the expanded device 102 in and relative to the thrombus 165.

Figure 18:
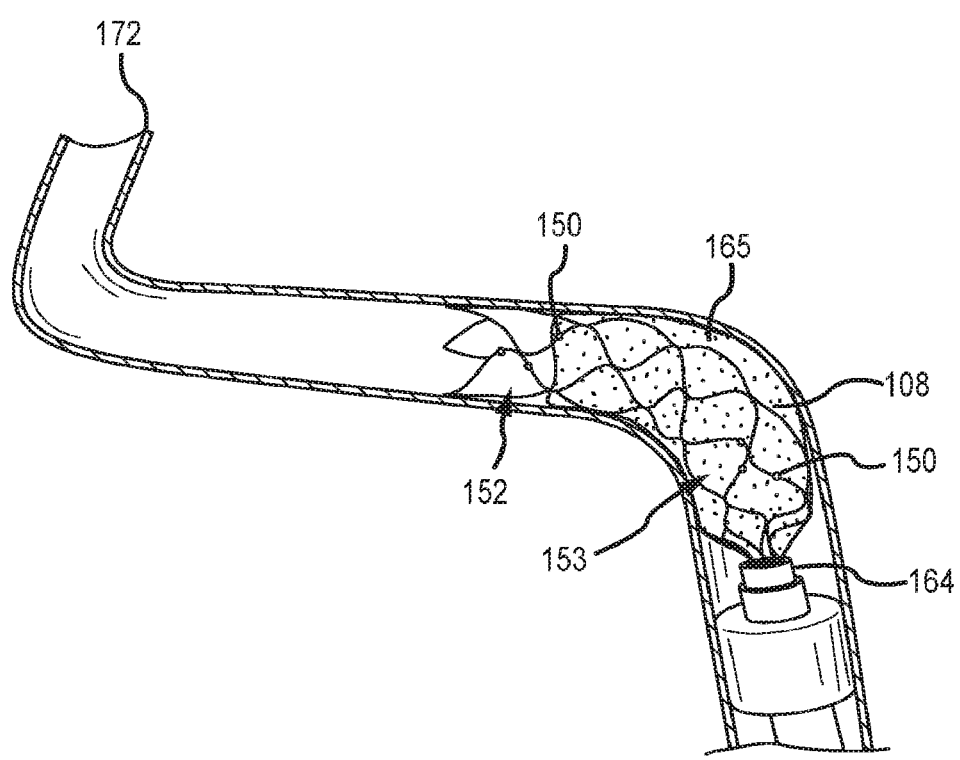

Referring to FIGS. 17 and 18, once the user is satisfied that the device 102 has been properly located longitudinally relative to the thrombus 165 and expanded into it, the thrombectomy device 102 can be withdrawn proximally, along with the thrombus 165. As illustrated in FIG. 18, the thrombectomy device 102 can be withdrawn proximally, along with the thrombus 165, into the guide catheter 164.

Figure 19:
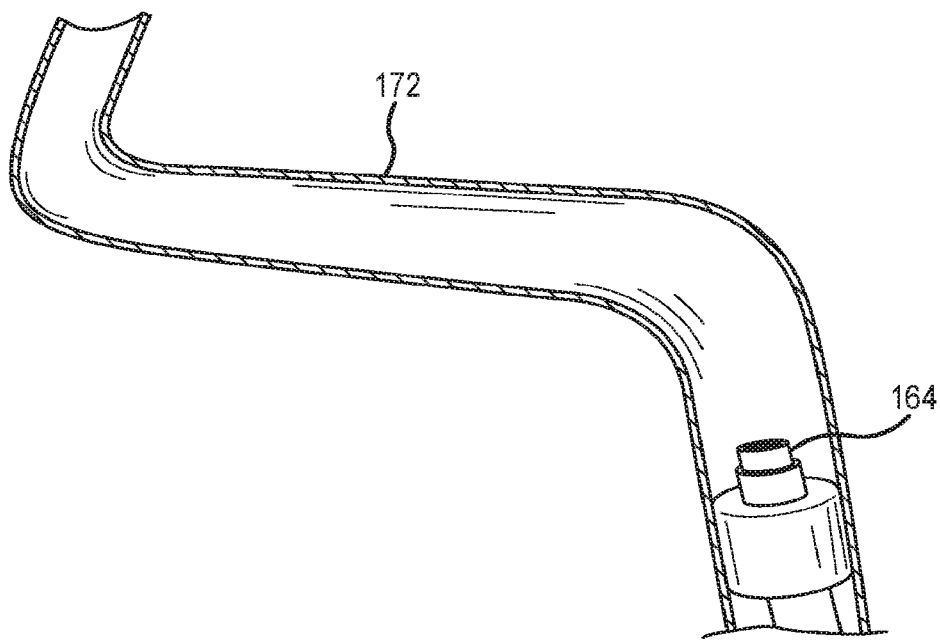
Figure 20:
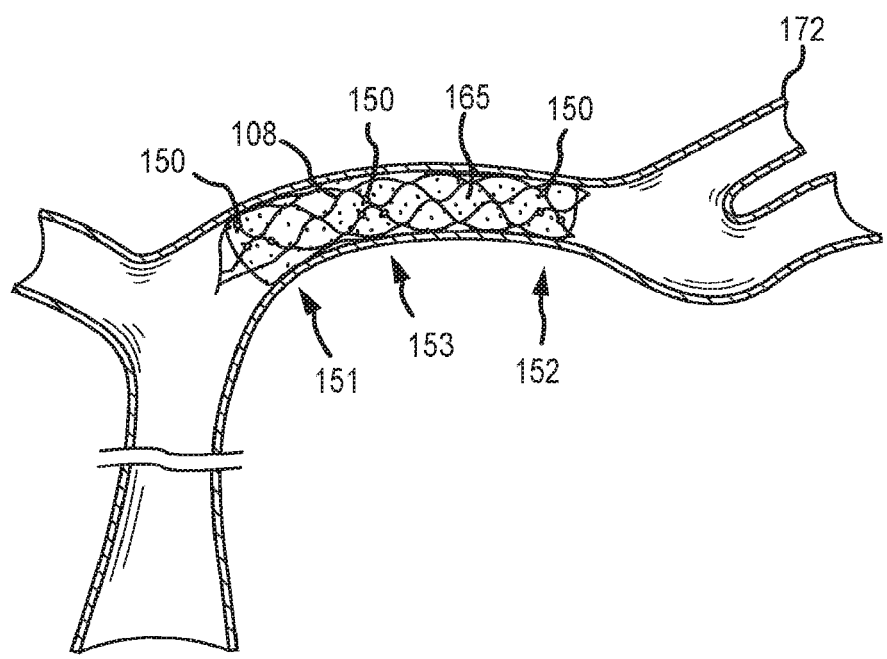

Referring to FIGS. 18 and 19, in embodiments wherein the guide catheter 164 comprises a balloon 168, the balloon optionally can be inflated to occlude flow during retraction of the thrombus 165 toward the guide catheter. Referring to FIG. 18, the thrombectomy device 102 is withdrawn proximally to the guide catheter 164. The guide catheter 164 causes the frame 108 to collapse, with the thrombus 165 engaged therein. The thrombus 165 is thus retrieved and removed from the anatomical vessel 172. Referring to FIG. 20, if retrieval of the thrombectomy device 102 is determined to be undesirable, e.g., to avoid damaging the vessel 172, and the thrombectomy device 102 is detachably or releasably connected to the manipulation member 104, the thrombectomy device 102 can be detached from the manipulation member 104 and can remain in the vessel 172.

Additionally, while the thrombectomy device 102 described above has been described in the context of use during a thrombectomy or blood flow restoration procedure, the thrombectomy device 102 can also, or alternatively, be used as an implantable member (e.g. stent). For example, the thrombectomy device 102 can be released through the connection 106 at a stenosis, aneurysm, or other appropriate location in a vessel. The thrombectomy device 102 can expand and engage a vessel wall so as to hold the vessel wall open and/or act as an occluding member. While the filament thicknesses, widths, cell sizes, and forces described above can be optimized for an thrombectomy device 102 for flow restoration, these values can also be optimized for a thrombectomy device 102 for use as an implantable member. In some embodiments the same values can be used for both flow restoration and use as an implantable member.

Also, while use of the thrombectomy device 102 described above with use of a catheter 107, the catheter 107 can be omitted in some embodiments.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplifying approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology.

A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more.

All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

We claim:

1. A method for engaging a thrombus, the method comprising:
   (a) advancing a thrombectomy device, using an elongate manipulation member, to a location radially adjacent to a thrombus in a blood vessel, the thrombectomy device comprising a working length and a non-working length, the non-working length comprising a mesh portion disposed between and separating the working length and a connection between the thrombectomy device and the elongate manipulation member, the non-working length having a connection marker disposed at the connection, the working length having a proximal end and a distal end with a plurality of proximal markers disposed at the proximal end, a plurality of distal markers, discrete from the proximal markers, disposed at the distal end, and a plurality of intermediate markers between the plurality of proximal markers and the plurality of distal markers;
   (b) positioning the thrombectomy device relative to the thrombus such that all of the proximal markers are proximal to or longitudinally aligned with a proximal end of the thrombus and all of the distal markers are distal to or longitudinally aligned with a distal end of the thrombus;
   (c), after (b), expanding the thrombectomy device into the thrombus;
   (d) imaging the proximal, intermediate, and distal pluralities of markers to (i) determine whether a maximum marker separation of the plurality of intermediate markers is less than a maximum marker separation of either the plurality of proximal markers or the plurality of distal markers, and (ii) determine a state of engagement of the working length with the thrombus based on the positioning of the proximal, intermediate, and distal pluralities of markers.

2. The method of claim 1, wherein, when the maximum marker separation of the plurality of intermediate markers is not less than the maximum marker separation of either the plurality of proximal markers or the plurality of distal markers, the method further comprises:
   collapsing the thrombectomy device;
   repositioning the thrombectomy device relative to the thrombus such that at least one of the plurality of proximal markers is proximal to or longitudinally aligned with a proximal end of the thrombus and at least one of the plurality of distal markers is distal to or longitudinally aligned with a distal end of the thrombus; and
   re-expanding the thrombectomy device into the thrombus.

3. The method of claim 1, wherein at least one of the proximal markers is located within 5 millimeters of the proximal end of the working length.

4. The method of claim 1, wherein the thrombectomy device includes a plurality of cells, and wherein the plurality of proximal markers is located within one cell-length of the proximal end of the working length.

5. The method of claim 1, wherein the thrombectomy device includes a plurality of arcuate marker-mounting projections.

6. The method of claim 5, wherein each of the proximal markers is disposed on one of the marking-mounting projections.

7. The method of claim 5, wherein each of the distal markers is disposed on one of the marking-mounting projections.

8. The method of claim 5, wherein each of the intermediate markers is disposed on one of the marking-mounting projections.

9. A method for engaging a thrombus, the method comprising:
   (a) advancing a thrombectomy device, using an elongate manipulation member, to a location radially adjacent to a thrombus in a blood vessel, the thrombectomy device comprising (i) a working length having a proximal end and a distal end with a plurality of proximal markers disposed at the proximal end, a distal marker at the distal end, and a plurality of intermediate markers distal of the plurality of proximal markers, and (ii) a non-working length comprising a mesh portion disposed between and separating the working length and a connection between the thrombectomy device and the elongate manipulation member, the non-working length having a connection marker disposed at the connection;
   (b) positioning the thrombectomy device relative to the thrombus such that all of the proximal markers are proximal to or longitudinally aligned with a proximal end of the thrombus;

(c), after (b), expanding the thrombectomy device into the thrombus;

(d) imaging the proximal plurality of markers, the intermediate plurality of markers, and the distal marker to (i) determine whether a maximum marker separation of the plurality of intermediate markers is less than a maximum marker separation of the plurality of proximal markers, and (ii) determine a state of engagement of the working length with the thrombus by observing the proximal plurality of markers, the intermediate plurality of markers, and the distal marker.

10. The method of claim 9, further comprising imaging the proximal end of the working length distinctly from the connection with the plurality of proximal markers.

11. The method of claim 9, wherein the thrombectomy device has a body comprising a plurality of struts, and the distal marker and plurality of proximal markers are more radiopaque than the body.

12. The method of claim 9, wherein at least one of the proximal markers is located within 5 millimeters of the proximal end of the working length.

13. The method of claim 9, wherein the thrombectomy device includes a plurality of arcuate marker-mounting projections.

14. The method of claim 13, wherein each of the proximal markers is disposed on one of the marking-mounting projections.

15. The method of claim 13, wherein each of the intermediate markers is disposed on one of the marking-mounting projections.

16. The method of claim 13, wherein the thrombectomy device comprises a plurality of struts forming a plurality of cells, and each of the arcuate marker-mounting projections extends from one of the struts.

17. The method of claim 9, wherein, when the maximum marker separation of the plurality of intermediate markers is not less than the maximum marker separation of the plurality of proximal markers, the method further comprises:

collapsing the thrombectomy device;

repositioning the thrombectomy device relative to the thrombus such that the plurality of proximal markers are proximal to or longitudinally aligned with a proximal end of the thrombus; and re-expanding the thrombectomy device into the thrombus.

18. The method of claim 9, wherein the thrombectomy device includes a generally cylindrical structure having overlapping edges in a roll-up configuration, and wherein expanding the thrombectomy device includes unrolling the device.

* * * * *